United States Patent [19]
Huse et al.

[11] Patent Number: 5,862,514
[45] Date of Patent: Jan. 19, 1999

[54] METHOD AND MEANS FOR SYNTHESIS-BASED SIMULATION OF CHEMICALS HAVING BIOLOGICAL FUNCTIONS

[75] Inventors: William D. Huse; Zhengxu He, both of Del Mar; Yifeng Wang, Mountain View, all of Calif.

[73] Assignee: Ixsys, Inc., San Diego, Calif.

[21] Appl. No.: 758,741

[22] Filed: Dec. 6, 1996

[51] Int. Cl.[6] .............................. G06F 19/00; G06F 17/00
[52] U.S. Cl. .................................... 702/22; 702/19; 528/1
[58] Field of Search .................................... 364/496, 497, 364/498, 499, 578; 702/22, 19; 528/1

[56] References Cited

U.S. PATENT DOCUMENTS 5,463,564  10/1995  Agrafiotis et al. ...................... 364/496

OTHER PUBLICATIONS

Foundations of Quantum Mechanics I, Ludwig, G., Springer–Verlag, New York, pp. 32–40, 1983.

Hendrickson, et al., The Syngen approach to synthesis design Analytica Chemica Acta v.1235, pp. 103–113, 1990.

*Primary Examiner*—Elizabeth Kemmerer
*Assistant Examiner*—Nirmal S. Basi
*Attorney, Agent, or Firm*—Baker & Maxham

[57] ABSTRACT

This invention provides a computer-executed method and means for simulating chemical synthesis. The invention concerns the simulation, by a programmed general purpose digital computer, of chemicals that have biological functions, and more specifically, concerns computer-implemented simulation of such chemicals based upon their synthesis and their assayed biological activity.

20 Claims, 3 Drawing Sheets

METHOD AND MEANS FOR SYNTHESIS-BASED SIMULATION OF CHEMICALS HAVING BIOLOGICAL FUNCTIONS

BACKGROUND OF THE INVENTION

1. Field of the Invention

The invention concerns the simulation, by a programmed, general purpose digital computer, of chemicals that have biological functions, and more specifically, concerns computer-implemented simulation of such chemicals based upon their synthesis and their assayed biological activity.

2. Description of the Related Art

Currently, there is no method or means for simulating the relationship between a chemical produced in a laboratory, a biological function of the chemical as experimentally measured in an assay, and the outcome of the experiment where the chemical is assayed. The ability to simulate such an experiment could vastly improve prediction of the outcome, enabling the use of the information developed in simulation to better identify and develop chemicals that will produce desired effects on selected biological receptors.

Currently, chemicals having biologically efficacious functions are synthesized from chemical libraries that contain huge numbers of chemicals. Based upon clinical structures, experience, intuition, or strictly random sampling, sets of chemicals are selected from a chemical library, and they are combined in chemical reactions subject to known reaction conditions to produce product chemicals. The biological function of the product chemicals is measured experimentally in an assay procedure, with the degree to which a product chemical achieves a desired biological function being indicated by a numerical value. After synthesis, thousands, or tens of thousands, of product chemicals may be assayed, with the assay results being determined and ranked by known means.

These large numbers of product chemicals are synthesized in order to discover one, or a few product chemicals that react with a protein to produce a desired effect, such as one that would inhibit or impair the progress of a disease. Assume that the disease is inhibited by attachment of an enzyme to a known location on the protein. The known location is called a "receptor site". Assume that attachment of a product chemical to the protein at receptor sites of interest inhibits enzyme attachment, thereby strongly indicating that the product chemical would also inhibit the progress of the disease. In this regard, attachment of the product chemical to a receptor site of interest would mimic the therapeutic effect of a (possibly scarce) naturally occurring compound. In this case, the product chemical would comprise a synthetic substitute for the scarce compound.

In any event, an assay may be conducted to determine whether, and to what extent, the product chemical binds to receptor sites of interest by coating a well or a container with the protein and then washing the protein with a solution containing the product chemical. Excess solution is emptied from the coated well and the compound for which a block, or substitute, is sought is "tagged" with another compound and, so tagged, is brought, in solution, against the protein. The extent to which the product chemical binds is evaluated by introducing another chemical that "develops" the tagging compound. In this regard, development activates the tagging compound in the sense that the tagging compound shows a certain color. Introduction of the protein to a spectrophotometer enables the detection of chemical activity by the measurement of color. Thus, if the tagged compound is not blocked, it will bind to the protein at the receptor sites and its presence will be indicated by the color of the tagging compound. If altogether blocked, the color of the tagging compound will not be detected at all or, if partially blocked, a smaller amount of the color will be detected.

Color-based assay techniques are well known, and apparatus are available to conduct photoassay of a great number of separate reactions. One such device is a spectrophotometer available from Molecular Devices that automatically conducts photoassay of a plurality of reactions in an array of reaction wells. Such a spectrophotometer can be coupled to a programmed, general purpose digital computer to process the results of an M×N array of reaction wells. For example, a MacIntosh brand computer available from the Apple Corporation, running the SOFTMX application program, also available from Molecular Devices, provides an output that presents photoassay results of a plurality of normalized assay result values, referenced to maximum and minimum values of a tagging color.

While the synthesis/assay process is well known and widely used, it is time-consuming and very manpower-intensive. To the extent that the process is iterative, because it is manually performed, desirable results emerge slowly, and patterns of desirable activity by product chemicals may be difficult to detect.

Manifestly, automated means and methods for simulating the direct synthesis/assay procedure have the potential of vastly increasing the speed of the process and quickly identifying patterns or trends of desirable results. However, to date only the evaluation phase of the assay step has been automated, and that only to a rudimentary degree. As yet, no effective mode of simulating the synthesis/assay process has emerged. Attempts have been made to create simulation models based upon molecular structure of product chemicals. However, such attempts have yet to find an effective model that links how a chemical is made and what its structure is, once synthesized. Accordingly, a manifest need exists for a method and means that simulate product chemicals in a way that directly reveals how they may be made and what their biological functions are.

SUMMARY OF THE INVENTION

This invention provides a method and a means that simulate product chemicals in terms of how they are made and the biological effects that they produce, thereby enhancing the efficiency with which drugs may be discovered and developed. Before the conception of this invention there was no way to mathematically represent a relationship between a chemical produced in a laboratory, a biological function of the chemical as experimentally measured in an assay, and the outcome of the experiment where the chemical is assayed. The invention is based on the inventors' mathematical model of the outcome of an assay experiment performed on a chemical synthesized according to a prescription of starting chemicals and reaction conditions.

An essential object of this invention is therefore to provide an alternative or an improvement to the prior art structure-based simulation model.

The invention is based upon the critical realization that synthesis and assay of a chemical may be statistically described as a physical system. Importantly, the synthesis of a chemical is modeled as a preparation procedure that is evaluated by a registration method. The preparation procedure is specifically modeled as a procedure by which a chemical is produced, while the registration procedure is modeled as an assay. Critically, there exists a function $\mu$ that underpins the description of a physical system modeled as a combination of the preparation and registration procedures.

The invention is embodied as a machine or as a machine-executed method for simulating chemical function using a database in which data representations of chemicals, data representations of synthesis procedures, and a set of functions representing assay procedures are stored. In this regard, a first set of first data structures representing chemicals of the chemical library is obtained from the database. A second set of second data structures representing industrially performable reactions by which chemicals represented by the first data structures are combined is also obtained from the database. The first and second sets are combined to produce a third set of data structures that represent experimentally performed, or hypothetically specified synthesis procedures in which chemicals in the chemical library and reactions in the reaction library are involved. The feasibility of a synthesis procedure represented by a third data structure is simulated by subjecting the third data structure to a function of the set of functions, such that the function produces a simulation value. A product chemical is synthesized according to the specified synthesis procedure and assayed to produce an assay result. The assay result is compared with the simulation value with reference to a tolerance limit, and another function may be selected from the set of functions based upon the comparison.

In this manner, a model simulating the synthesis and assay of large numbers of product chemicals can be evaluated and adaptively reconfigured by testing against actual synthesis/assay results produced from a much smaller set of product chemicals.

DETAILED DESCRIPTION OF THE PREFERRED EMBODIMENTS

Figure 1:
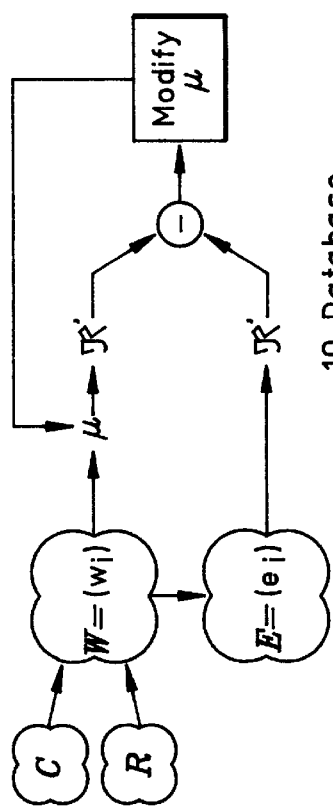
FIG. 1 illustrates an iterative process for composing a function $\mu$ that predicts the feasibility of a specified synthesis procedure in addition to the biological function of the produced chemical.

With reference to FIG. 1, assume a collection of available chemicals, denoted by C, and a collection of reactions which are industrially performable, denoted by R. A chemical compound, w, which is synthesized from a set of chemicals C'⊆C through a list of reactions R'⊆R is denoted by w(C', R').

A traditional synthesis/assay process that leads to drug discovery is described by the pseudocode in Table 1. The synthesis and assay in this process are actually-performed procedures. With large C and R, this enumeration-styled process is very time- and fund-consuming.

TABLE 1

Pseudo Code Representing Traditional Drug Discovery (1) Given C and R
(2) for any C'⊆C and R'⊆R do
(3)    begin
(4)    ω = Synthesis (C', R'), performed in chemical laboratory;
(5)    $\Re$ = Assay (ω(C',R')), performed in assay laboratory;
(6)    if ($\Re$ > ζ), where ζ is a threshold of acceptability
(7)      announce ω(C', R') as a new drug;
(8)    end for With our invention, regularities between $\Re$, C and R are found. We represent the relationship between them by the mathematical formula of equation (1).

$$\Re' = \mu(w) \qquad (1)$$

In equation (1) $\Re'$ represents the result of a simulated assay of a simulated product chemical w. Based on quantum theory, the mathematical function $\mu$ (hereinafter, the "prediction function") is likely to be decomposed into a set of sub-functions, $\mu_i$, i=1, . . . , n, each of which describes one aspect of this problem (a quantum dimension):

$$\Re' = \sum_i \lambda_i \times \mu_i(w) \qquad (2)$$

This mathematical function $\mu$ is composed based on actual experimental data E obtained by synthesis and assay, where, E={$e_i$=($w_i$, $\Re_i$)|$\Re_i$=Assay($w_i$), i=1, 2, . . . }. The composition of the function $\mu$ is depicted by FIG. 1 and described by the pseudo code in Table 2. If the computation results obtained by $\mu$ match the experimental results within a range of tolerance that lies between 0 and a tolerance limit, it is determined that a prediction function has been identified that may reliably predict drug discovery. In this regard, $\mu$ is a "prediction" function in that it predicts the feasibility of a specified synthesis procedure in addition to the biological function of the chemical(s) produced according to the procedure.

Now, assume composition of a reliable prediction function $\mu$. Before real synthesis and assay experiments are performed respectively in a chemical laboratory and assay laboratory, the invention composes a drug which is most likely to be synthesizable and have a particular biological effect of interest. This process, picking out the most promising drug composition solution from the vast fabricated chemical compound library, is an optimization process, and is illustrated by the pseudocode given in Table 3.

TABLE 2

Iterative Composition Of Function $\mu$ (1) Initially composing function $\mu$;
(2) for every e ∈ E do
(3)    being
(4)    $\Re'$ = $\mu$(e.ω);
(5)    if (|$\Re'$ – e.$\Re$| > tolerance 1 unit) begin
(6)      modifying function $\mu$;
(7)      goto step 2;
(8)    end if;
(8)    end for;
(9) announce $\mu$ is reliable up to now.

TABLE 3

(Prediction + Experiment) Discovery Process (1) Given C and R;
(2) In the solution space, C×R, looking for (C', R')s where
    $\Gamma = \{(C', R') | C' \subseteq C \text{ and } R' \subseteq R \text{ and } \mu(\omega(C', R') > \zeta\}$
(3) for every (C', R') ∈ Γ do
(4)     begin
(5)     ω = Synthesis (C', R');
(6)     $\Re$ = Assay(ω(C',R'));
(7)     E = E∪{(w, $\Re$)};

TABLE 3-continued (Prediction + Experiment) Discovery Process (8)     if ($\Re$ > ζ) announce success;
(9)     end for;

Actually, during the utilization of the prediction function, the prediction function will also be optimized due to access to more experimental data becoming available (E expends during this process).

2. Composition of the database

Figure 2:
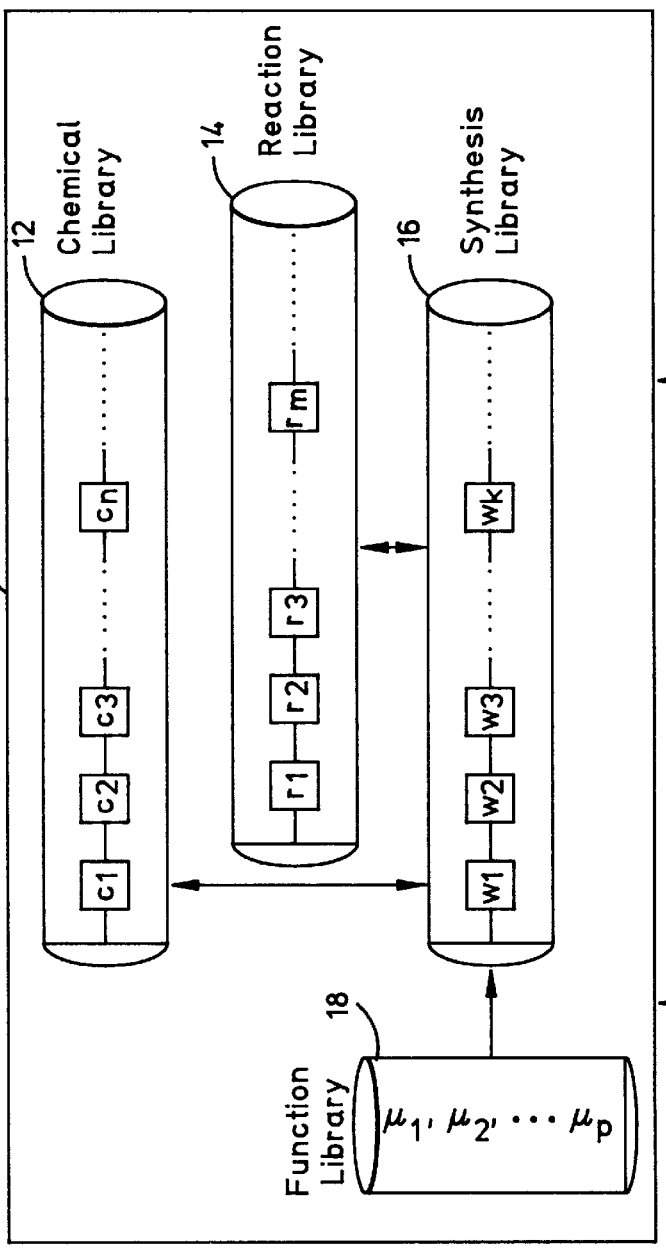
FIG. 2 is a block diagram of a database used in the invention.

In order to manage the data and information used in this invention in a way sufficient for prediction function development and for drug discovery optimization, we have designed a database 10 that is illustrated in FIG. 2.

The database 10 comprises four libraries: a chemical library 12, a reaction library 14, a synthesis library 16, and an analysis function library 18.

| | |
|---|---|
| chemical library 12: | contains entries describing all chemicals available for a task and corresponding structural information, chemical and physical properties of the chemicals. |
| reaction library 14: | each entity in the library is a set of reaction conditions applied to a synthesis process, such as temperature, densities of reagents, solution type, etc. |
| synthesis library 16: | each entity in the library is a tree structure graph modeling a synthesis procedure that may produce a product chemical. Note that the entities of this library are represented by w. In this regard, w represents a synthesis procedure generally, and may specifically represent a product chemical produced by a represented synthesis procedure. |
| analysis function library 18: | the functions in this library are applied to the contents of the synthesis library to calculate predetermined parameters of modeled product chemicals. |

All of these libraries are updatable and extendable either by known maintenance means, by a user, or both.

3. The data structures of the entities in the database

The data structures of entities of the database directly determine the time and space (memory) efficiency of the database.

(1) Chemical library (C) 12:

$C = \{c_1, c_2, c_3, \ldots, c_{11}, \ldots\}$

The chemical library 12 is a first set of first data structures, each representing an entity in the library, wherein each entity in the chemical library is a chemical, represented by a list of properties, such as molecular geometry, bond length and bond angles, molecule weight, and so on.

The chemicals can be classified into many categories in terms of the type of tags in molecular structure.

$\forall c_i \in C$, can be represented as a first data structure, which may be treated as an instance of an object, as follows:

```
typedef struct Chemical{
    int ID;                              /* ID of this reagent */
    char chemical_name[20];              /* name of the chemical */
    char *formula;                       /* structural formula */
    void *properties;                    /* properties of the chemical */
    struct synthesis_list *synthesises;  /* list of synthesis processes involved */
    struct Chemical *next;               /* next chemical instant */
} CHEMICAL;
```

(2) Reaction library (R) 14:

The reaction library 14 comprises a set of second data structures, each representing an entity of the library wherein each entity of R may represent necessary conditions for an industrially performable reaction.

$R = \{r_1, r_2, \ldots, r_m, \ldots\}$ $\forall r_i \in R$, is represented as a second data structure, which may be treated as an instance of an object described as follows:

```
typedef struct Condition {
    void *condition_1;
    void *condition_2;
    .
    .
    .
    void *condition_q;
    struct synthesis_list *sunthesises;
    struct Condition *next;
} CONDITION;
```

(3) Synthesis library (w) 16:

$W = \{w(C',R') | C' \subseteq C \text{ and } R' \subseteq R\}$

Figure 3:
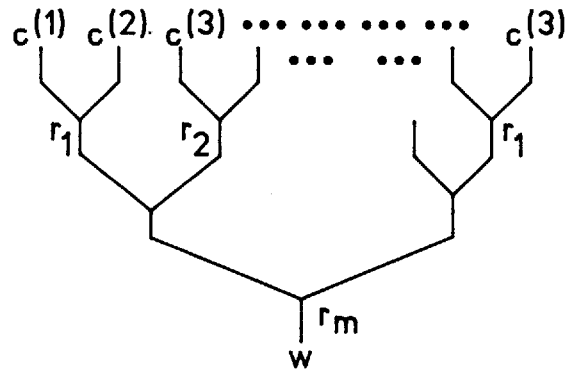
FIG. 3 illustrates a tree that represents a reaction sequence by which a product chemical is synthesized.

The synthesis library 16 comprises a set of third data structures, each representing an entity of the library wherein each entity w ∈ W represents a reaction sequence which can be represented as a tree-shaped graph as shown in FIG. 3.

Figure 4A:
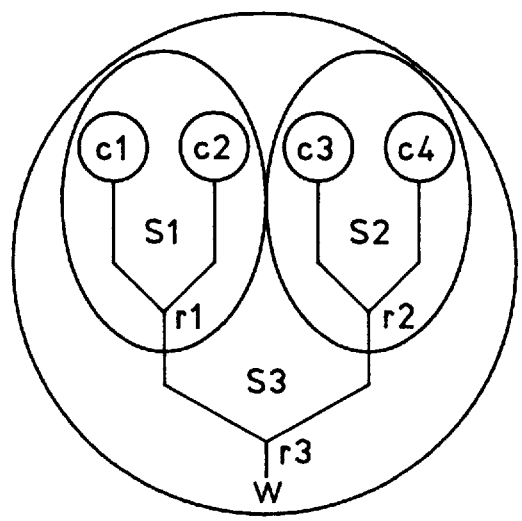
FIGS. 4A and 4B illustrate how a synthesis tree representing synthesis of a product chemical may be iteratively described.
Figure 4B:
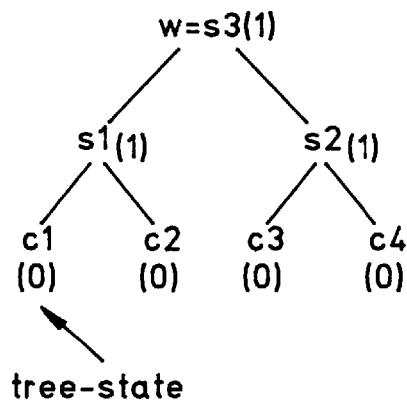

This synthesis tree can be expressed in an iterative way by means of an object defined as follows:

```
typedef struct synthesis_tree {
    int tree_state;
    struct chemical *c;
    struct synthesis_tree *subtrees[N];
    struct condition *r;
} SYNTHESIS_TREE
``` if tree_state=0, this tree is actually a chemical reagent (c) instead of a synthesis tree. Otherwise, it is a sub-tree. For example, FIGS. 4A and 4B illustrate a synthesis tree's iterative description.

(4) Function library 18:

As to a hypothetically specified synthesis w, the invention predicts its feasibility and other properties through mathematical analysis based on the quantified parameters of the synthesis and involved chemicals. In other words, a mathematical function is composed, as follows:

$$\Re'=\mu(w)$$

where $\Re'$ is a random variable representing some kind of probability of something.

The prediction function $\mu$ can be decomposed into a collection of relatively simple sub-functions $(\mu_1, \mu_2, \ldots, \mu_p)$:

$$\mu = F(\mu_1, \mu_2, \ldots, \mu_p)$$

Each sub-function, say $\mu_i$, takes a synthesis tree (w) as its argument. All sub-functions $\mu_i$ are pre-defined and assigned a unique name that enables use of the sub-function in the invention. The data structure for this library is defined as follows:

```
typedef of struc sub function {
    char func_name[20]'
    void *return_value;
    void (*pf)( );
    struct sub-function *next;
} SUB-FUNCTION
```

A dedicated language may be provided for composition of a formula expression using the functions in the function library 18. For example, assume composition of a formula as follows:

$$F = \alpha_1 \times \mu_1 + \alpha_2 \times \mu_2 + \ldots + \alpha_n \times \mu_n$$

$\mu_i \in$ function library $\alpha_k$ is a coefficient

Automated database processing may automatically apply this formula to a candidate syntheses tree in the synthesis library 16, and compare the computational results with experimental results. The formula can be dynamically modified to approach the experimental data.

Industrial Application

Figure 5:
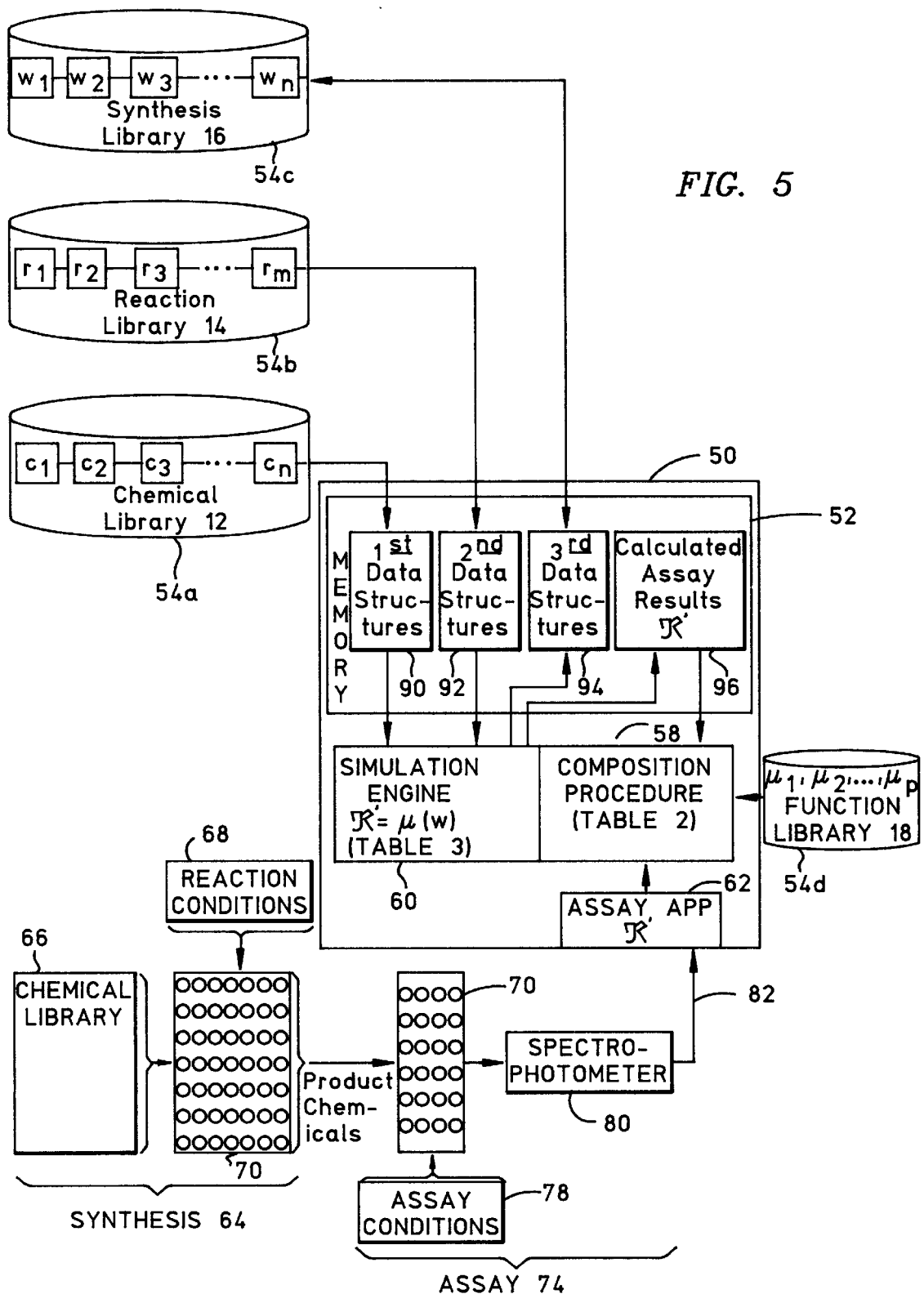
FIG. 5 illustrates a combination including a programmed, general purpose digital computer, the database of FIG. 2, and a synthesis/assay procedure by which the invention is practiced.

FIG. 5 is an illustration of an industrial application of the invention in which a programmed, general purpose digital computer 50 having standard hardware and software components, including a memory 52, is conventionally coupled to a storage facility that may include, for example, a direct access storage system including components 54a, 54b, 54c and 54d. The components 54a–54d of the storage facility are used to store the storage library illustrated in FIG. 2. The storage facility is shown as comprising individual components 54a–54d only for purposes of illustrating the library architecture of the database shown in FIG. 2. Relatedly, the storage facility component 54a includes the chemical library 12, the storage facility component 54b has stored in it the reaction library 14, the storage facility component 54c provides storage capacity for the synthesis library 16, while the storage facility component 54d stores the functions that make up the function library 18.

The programmed, general purpose digital computer ("computer") 50 is programmed in a conventional way to execute one or more computer programs that embody the pseudocode of Tables 2 and 3. In this regard, Tables 2 and 3 are embodied as a composition procedure 58 and a simulation engine 60 that may comprise, for example, one or more computer software programs that include program code in compiled, assembled and linked form that cause the computer 50 to perform the functions embodied in the pseudocode of Tables 2 and 3.

Embodiment of the invention in the industrial application of FIG. 5 includes programming the computer 50 with an assay application 62 that receives and processes experimentally-derived assay results from an actually-performed synthesis/assay procedure 64, 74.

The synthesis/assay procedure 64, 74 includes the steps of selecting chemicals from a chemical library 66, and subjecting the chemicals to reaction conditions 68 in a synthesis laboratory to produce a plurality of product chemicals 70. In FIG. 5, the plurality of product chemicals are represented as an M×N array. In an assay laboratory, the assay step 74 includes subjecting the product chemicals 70 to assay conditions 78, with assay results being measured by a spectrophotometer 80 from which assay results are provided at 82 as an input to the assay application 62.

In operation, the function $\mu$ is composed according to procedures set forth in Table 2. Table 2 takes experimental results derived from synthesis/assay of one or more product chemicals. Each of these results is represented by a respective assay result $\Re_i$. Each assay result is a measure of biological activity of a particular product chemical represented by a synthesis tree $w_i$. In this regard, during the iterative composition of the function $\mu$, each $w_i$ comprises a third data structure 94 that is composed in the memory 52 by combining first data structures 90 obtained from the chemical library 12 with second data structures 92 obtained from the reaction library 14, where the first data structures 92 represent chemicals of the chemical library 66, while the second data structures represent reaction sequences 68 by which chemicals represented by the first data structures are combined to produce product chemicals whose assays are represented by the input 82 to the assay application 62. Thus, during composition of the function $\mu$, there is, (for each specified synthesis procedure $w_i$) a particular assay result $\Re_i$ comprising actual experimental results produced by the synthesis/assay procedure 64, 74. Thus, in line (4) of Table 2, a calculated assay result $\Re'_i$ is obtained and stored at 96 in the memory 52 for the third data structure instance of $w_i$ that corresponds to a synthesis procedure that produces a product chemical w for which the assay result $\Re_i$ has been obtained. In line (5) of Table 2, the absolute value of the difference between the simulated assay value $\Re'_i$ and the product of $e_i$ and $\Re_i$ is compared to a tolerance limit. If the absolute value of the difference is not greater than the tolerance limit, the function $\mu$ is deemed reliable. It may equivalently be stated that if the absolute value of the difference is less than or equal to the tolerance limit, the function $\mu$ is deemed reliable. Otherwise, the function is modified by selection of another function from the function library 18 and another iteration of the composition procedure in Table 2 is executed.

When a reliable function $\mu$ is found, this is deemed the "simulation function". The simulation function is used by the simulation engine 60 to execute the procedure of Table 3. In Table 3, a subset $\Gamma$ of the solution space C×R is obtained, with members of the solution space combined as described above to produce the subset as a set of third data structures, each in the form, preferably, of the synthesis tree described above, which are subjected to the simulation function. In this regard, each synthesis tree represents a product chemical, while the simulation function represents an assay performed on the set of product chemicals represented by the third data structures. For each synthesis tree, Table 3 obtains a solution to equation (1) and compares it to tolerance value $\zeta$. For every synthesis tree that produces an equation (1) result that exceeds the tolerance value, the simulated chemical is synthesized, assayed, and if the assay result exceeds the tolerance value, the product chemical is deemed successful.

During the iterative composition of the function $\mu$ (Table 2) and during the discovery process of Table 3, the synthesis library 16 is built, with each third data structure stored in the library representing a product chemical. Each third data structure may be stored with a value representing the actual experimentally-determined assay result for the represented product chemical. Eventually, the synthesis library 16 will be deep and broad enough to be mined for function trends leading to the rapid discovery of product chemicals that exhibit desirable functions.

Function Composition

1. Quantum Theory and Structures of Molecules

Quantum theory originated from the study of atoms or small molecules, and other small physical systems. The formulation of the theory took several decades of active research to get complete.

The structures of molecules can be computed using the equations of Quantum Theory. The mathematical equation representing the theory (most notably the Schrodinger equation), although difficult to study, has been approached by various methods (e.g., electron orbital theory, Hartree Fock theory), giving meaningful approximations to the molecular structures. Actually, exact solutions are found only in very simple cases, in which only a handful of electrons are involved.

The study of structures is still a very active field of research. It has proved to be very useful in predicting the chemical reactions among the micro-molecules.

2. Structure-Based Prediction

There are many works in the direction of a structural approach in predicting the ligand binding of G-protein coupled receptors. Here the ligand is usually a micro-molecule, but the protein-receptor consists of a formation of macromolecules.

There have been attempts to set up a Hamiltonian for the macrosystem. The Hamiltonian for the macrosystem could be useful in predicting qualitative properties or the values of statistical physics quantities.

Assume that the Hamiltonian formula is correctly worked out. Trying to exactly solve a system containing thousands of electrons under one Hamiltonian not only is beyond the present (or near future) mathematical computational ability, but also could be meaningless. One reason is that is could take too long for the system to go from an arbitrary state to the ground state (or some more or less stable state), and the process could be disturbed by many small random factors. So even if the ground state is the most probable state, the probability density in its neighborhood could still be too small to count.

Another way to attack the problem is to study chemical reactions between a ligand and local region of the macromolecule. That is, set up a local Hamiltonian which involves a ligand, and the local part of the macromolecule. One may develop a parallel theory in the local region. However, we should point out that although this is similar to the Hamiltonian of microsystems, the problem could be substantially more difficult as there is no clear cut limit for the local region.

There have been none to rare reports of positive results in these directions.

3. Alternates to the Structural Approach

It is an open question if the quantum theory of atoms and molecules, reasonably correct for small systems, also works for macrosystems.

Since the "potential ligands" are small molecules, their structures can be worked out reasonably well by theoretical computations (using the method of X-ray crystallography). Many invariants could be defined: from the geometric structures of the configuration of atoms, the wave (and spin) function of electrons, to the measures of electromagnetic vibrations of atomic nuclei, and functions derived from these.

Assuming that the structural approach works, some of these structural parameters may be correlated with the experimental outcome of the prediction function $\mu$. If consistent correlation can be detected, then regression models could be used in predicting the outcome of $\mu$ (with probability) for other potential product chemicals.

Many parameters may be used for the prediction function. Following are examples of a few, out of hundreds of structural or non-structural parameters.

(i) Let I denote the measure of inertness of the potential product chemical. Consider, as an example, the following simple linear regression model:

$$\mu = b + c_1 I + c_2 I^2 \epsilon_1$$

where $c_1$ and $c_2$ are constants, $\epsilon$ is a random variable (the error term). The constants $c_1$ and $c_2$ can be determined by some routine calculation, based on the method of best square mean approximation.

(ii) Consider the invariants of the 3D geometric structure, such as diameter, volume, density, shape of its boundary, and functions of these. Examples:

$$e = \frac{\text{volume}}{\text{diameter}^3};$$

$$B = \frac{\text{boundary area}}{\text{diameter}^2}.$$

These parameters may be used in the following model:

$$\mu = b_1 + c_3 e + \epsilon,$$

or $$\mu = b_2 + c_4 B + \epsilon.$$

(iii) From the electron orbital theory, each electron is associated with four quantum numbers: n, l, $m_s$, and s.

For each set (n, l, $m_s$, s), define the following functions. Let N(n, l, $m_s$, s) be the number of electrons whose quantum numbers are given by the quadruple, and for each of these N electrons, let E denote the total energy of the electron (including the potential energy with respect to the atoms), and let P be the distance from the boundary of the effective region of the electron to the boundary of the molecule.

Note that E and P could be regarded as a collection of variables indexed by the (n, l, $m_s$, s) and k, where k=1, 2, . . . , (n, l, $m_s$, s). Let J be the collection of the indices (n, l, $m_s$, s, k), then, $E_i$, $P_i$ will be used to denote all of these variables.

One may define an order of these indexes in J, according to, say, the energy E. In fact, we can assume J is fixed: just let E and $P_i$ be some adjustable small, negative numbers, if the electron does not exits. The assumption here is that electrons of relatively low energy level are less likely to be free.

This suggests another regression model:

$$\mu = b + \sum_{i \in j} c_i E_i + \sum_{i \in j} d_i P_i + \epsilon;$$

where $\alpha_i$, $\beta_i$, $c_i$ and $d_i$ are all constants, to be determined by the least square method, and $\epsilon$ is a random variable.

4. Use of Synthesis Tree According to the Invention

The parameters introduced in section 3 may be defined for each component in the synthetic tree where each component is indexed by $k \in K = \{1, 2, \ldots, n\}$. For each k, we may use the method of 3 for a prediction model:

$$\mu = \mu_k = b_o + \alpha_k x_k + \epsilon_k; \quad (4.1)$$

where $\alpha_k$ is a constant vector, and $x_k$ is a vector variable. We then combine these, and do a search:

$$\mu = b + \sum_{k \in K} c_k x_k + \epsilon$$

Or, more generally, $$\mu = b + \sum_{k \in K} c_k x_k + \sum_{i, k \in K} c_{ik}[x_k \otimes x_i] + \epsilon;$$

where $[x_k \otimes x_i]$ denotes the vector each of whose coordinates is the product of a coordinate of $x_k$ and a coordinate of $x_i$.

The most general formulation is:

$$\mu = b + \sum_{k \in K} c_k x_k + \quad (4.2)$$

$$\sum_{i, k \in K} c_{ik}[x_k \otimes x_i] + \ldots + c_{12\ldots n}[x_1 \otimes x_2 \otimes \ldots \otimes x_n] + \epsilon.$$

We note that this last formula reduces to (4.1) once all but one variables are fixed. Thus, in a way, for each $k \in K$, the constants $b_k$, $\alpha_k$ of (4.1) are related to the constants $c_k$, $c_{ik}$, … in (4.2)

5.0 Alternate Embodiment of Function Composition

A prediction function for $\mu$ may be constructed, using regression analysis, and based upon the experimental data, $e$, $\Re$, $e \in E$. In this regard, a regression model, denoted by M, will have the following form:

$$\mu = \sum_{i=1}^{n} c_i x_i + \epsilon \quad (5.0)$$

where $x_i = x_i(w)$'s are the parameters used in the model, $c_i$'s are the constants whose optimal values are determined by regression analysis (e.g. the method of least square means), and $\epsilon$ is the random error term. We assume a collection of such models.

The procedure in finding the prediction function $\mu$ then consists of two steps.

Step 1: For each regression model M, as in (5.0), minimize the following functional:

$$\sum_{e \in E} \left| e \cdot \Re - \sum_{i=1}^{N} c_i x_i(ew) \right|^2,$$

over $$(c_1, c_2, \ldots, c_n) \in \mathbb{R}^N,$$

Where $\mathbb{R}$ is the set of real numbers. Now, let $(\bar{c}_1, \bar{c}_2, \ldots, \bar{c}_n)$ denote the minimizer, and let:

$$\text{Error}(M) = \sqrt{\sum_{e \in E} \left| e \cdot \Re - \sum_{i=1}^{N} \tilde{c}_i x_i(ew) \right|^2},$$

Step 2: Compare Error(M) for different regression models M. Pick the one, say $\tilde{M}$, so the Error $(\tilde{M})$ is the smallest. Then announce the choice of prediction function $$\mu \sum_{i=1}^{\tilde{N}} \tilde{c}_i \tilde{x}_i,$$

where $\tilde{x}_1, \tilde{x}_2, \ldots, \tilde{x}_{\tilde{N}}$ are the parameters used in $\tilde{M}$, and ($\tilde{c}_1, \tilde{c}_2, \ldots, \tilde{c}_{\tilde{N}}$) is the optimizer obtained in Step 1 for the model $\tilde{M}$.

In other words, the alternate emboidment of the procedure for function composition is:

Step 1: Optimize the coefficients $(c_1, c_2, \ldots, c_n)$

Step 2: Choose the best regression model.

Other embodiments and modifications of this invention may occur to those of ordinary skill in the art in view of these teachings. Therefore, this invention is to be limited only by the following claims, which include all such embodiments and modifications when viewed in conjunction with the above specification and accompanying drawings.

We claim:

1. A computer-executed method for simulating chemical synthesis using a database in which data representations of chemicals and data representations of product procedures are stored, comprising:

obtaining from the database a first set of first data structures representing chemicals of a chemical library;

obtaining from the database a second set of second data structures representing reactions by which chemicals represented by the first data structures are combined;

combining the first and second sets to produce a third set of data structures that represent synthesis procedures;

synthesizing one or more product chemicals by combining chemicals represented by the first data structures according to reactions represented by the second data structures;

assaying the one or more product chemicals to provide assay results;

followed by:

(a) simulating the feasibility of one or more synthesis procedures by subjecting third data structures to a simulation function of a set of simulation functions, the simulation function producing one or more simulation values;

(b) establishing a tolerance limit relating to the difference between the assay results and one or more simulation values;

(c) comparing the assay results with the one or more simulation values with reference to the tolerance limit;

(d) based upon the comparison, selecting another simulation function from the set of simulation functions; and repeating steps (a), (b), (c), and (d) until the result of the comparison is less than or equal to the tolerance limit.

2. The method of claim 1, wherein assaying includes assaying biological activity of the one or more product chemicals.

3. The method of claim 1, wherein combining includes producing said third set of data structures such that each third data structure comprises a tree-shaped graph.

4. The method of claim 1, wherein combining includes producing said third set of data structures such that each third data structure comprises a synthesis tree.

5. The method of claim 1, wherein simulating feasibility includes producing a simulation value ($\Re'$) by subjecting each third data structure (w) to a prediction function ($\mu$), according to:

$$\Re' = \mu(w).$$

6. The method of claim 5, wherein the prediction function $\mu$ is decomposed into a set of subfunctions ($\mu_1, \mu_2, \ldots, \mu_p$), and wherein each sub-function ($\mu_1, \mu_2, \ldots, \mu_p$) takes a synthesis tree (w) as its argument.

7. A system for simulating chemical synthesis, comprising:

a database with:
  a chemical library containing first data structures representing chemicals;
  a reaction library containing second data structures representing reactions by which chemicals represented by the first data structures are combined; and
  a synthesis library containing third data structures representing synthesis procedures;

means for combining said first data structures with said second data structures to produce said third data structures; and means for:
  receiving assay results obtained by assaying one or more product chemicals synthesized by combining chemicals represented by the first data structures according to reactions represented by the second data structures;
  simulating the feasibility of one or more synthesis procedures by subjecting third data structures to a simulation function of a set of simulation functions, the simulation function producing one or more simulation values;
  establishing a tolerance limit relating to the difference between the assay results and one or more simulation values;
  comparing the assay results with the one or more simulation values with reference to the tolerance limit; and
  based upon the comparison, selecting another simulation function from the set of simulation functions until the result of the comparison is less than or equal to the tolerance limit.

8. The system of claim 7, further including an apparatus for providing said assay results.

9. The system of claim 7, wherein the assay results indicate biological activity of the one or more product chemicals.

10. The system of claim 7, wherein the means for combining produces said third set of data structures such that each third data structure comprises a tree-shaped graph.

11. The system of claim 7, wherein the means for combining produces said third set of data structures such that each third data structure comprises a synthesis tree.

12. The system of claim 7, wherein simulating feasibility includes producing a simulation value ($\Re'$) by subjecting each third data structure (w) to a prediction function ($\mu$), according to:

$$\Re' = \mu(w).$$

13. The system of claim 12, wherein the prediction function $\mu$ is decomposed into a set of subfunctions ($\mu_1, \mu_2, \ldots, \mu_p$), and wherein each sub-function ($\mu_1, \mu_2, \ldots, \mu_p$) takes a synthesis tree (w) as its argument.

14. A system for testing results ("assay results") of assaying product chemicals synthesized by combining chemicals according to reaction sequences comprising:

a database with:
  a chemical library containing first data structures representing said chemicals;
  a reaction library containing second data structures representing reactions by which said chemicals are combined in said reaction sequences; and
  a synthesis library containing third data structures representing synthesis procedures;

means for combining said first data structures with said second data structures to produce said third data structures; and means for:
  (a) simulating the feasibility of one or more synthesis procedures by subjecting third data structures to a simulation function of a set of simulation functions, the simulation function producing one or more simulation values;
  (b) establishing a tolerance limit relating to the difference between the assay results and one or more simulation values;
  (c) comparing the assay results with the one or more simulation values with reference to the tolerance limit; and
  (d) based upon the comparison, selecting another simulation function from the set of simulation functions unless the result of the comparison is less than or equal to the tolerance limit.

15. The system of claim 14, further including an apparatus for providing said assay results.

16. The system of claim 14, wherein the assay results indicate biological activity of the one or more product chemicals.

17. The system of claim 14, wherein the means for combining produces said third set of data structures such that each third data structure comprises a tree-shaped graph.

18. The system of claim 14, wherein the means for combining produces said third set of data structures such that each third data structure comprises a synthesis tree.

19. The system of claim 14, wherein simulating feasibility includes producing a simulation value ($\Re'$) by subjecting each third data structure (w) to a prediction function ($\mu$), according to:

$$\Re' = \mu(w).$$

20. The system of claim 19, wherein the prediction function $\mu$ is decomposed into a set of subfunctions ($\mu_1, \mu_2, \ldots, \mu_p$), and wherein each sub-function ($\mu_1, \mu_2, \ldots, \mu_p$) takes a synthesis tree (w) as its argument.

* * * * *